United States Patent [19]

Ohta et al.

[11] Patent Number: 5,189,209
[45] Date of Patent: Feb. 23, 1993

[54] PROCESS FOR PRODUCING HIGHLY PURE ISOPHTHALIC ACID

[75] Inventors: Tazuo Ohta, Tokyo; Kazuo Tanaka, Okayama; Fumio Ohgoshi, Okayama; Terumasa Yoshida, Okayama; Ichihei Motoyama, Okayama, all of Japan

[73] Assignee: Mitsubishi Gas Chemical Company, Inc., Japan

[21] Appl. No.: 701,853

[22] Filed: May 17, 1991

[30] Foreign Application Priority Data

May 17, 1990 [JP] Japan .................. 2-125437

[51] Int. Cl.$^5$ .................. C07C 51/265; C07C 51/487
[52] U.S. Cl. ...................................... 562/414; 562/487
[58] Field of Search ........................... 562/414, 487

[56] References Cited

U.S. PATENT DOCUMENTS

| | | | |
|---|---|---|---|
| 3,974,214 | 8/1976 | Worrell et al. | 562/412 |
| 4,259,522 | 3/1981 | Hanotier | 562/412 |
| 4,675,438 | 6/1987 | Schwartz et al. | 562/416 |
| 4,827,026 | 5/1989 | Brugee et al. | 562/416 |
| 4,933,492 | 6/1990 | Schroeder et al. | 562/487 |
| 4,937,378 | 6/1990 | Schroeder | 562/487 |

FOREIGN PATENT DOCUMENTS

| | | |
|---|---|---|
| 1056319 | 12/1964 | United Kingdom . |
| 1152575 | 5/1969 | United Kingdom . |
| 1152576 | 5/1969 | United Kingdom . |
| 1555246 | 11/1979 | United Kingdom . |
| 1577544 | 10/1980 | United Kingdom . |

*Primary Examiner*—Paul J. Killos
*Assistant Examiner*—Vera C. Clarke
*Attorney, Agent, or Firm*—Venable, Baetjer, Howard & Civiletti

[57] ABSTRACT

A process for producing highly pure isophthalic acid which comprises (a) carrying out liquid phase oxidation of an m-dialkyl benzene with molecular oxygen in an acetic acid solvent in the presence of a heavy metal catalyst to form crude isophthalic acid, (b) contact-treating the resulting crude isophthalic acid with a noble metal catalyst belonging to the Group VIII of the Periodic Table supported by activated carbon in the presence of hydrogen, and then (c) separating the deposited isophthalic acid crystal and (d) filtration-treating the separated mother liquor and (e) recirculating the mother liquor thus treated into the liquid phase oxidation step (a) for reusing as a solvent in step (a) is disclosed.

6 Claims, No Drawings

PROCESS FOR PRODUCING HIGHLY PURE ISOPHTHALIC ACID

BACKGROUND OF THE INVENTION

This invention relates to a process for producing highly pure isophthalic acid which is useful as an intermediate for preparing polymers, such as an unsaturated polyester resin, alkyd resin and thermal resistant polyamide, etc., and particularly relates to a process for producing highly pure isophthalic acid which comprises hydrogenating the impurities contained in crude isophthalic acid which has been obtained by liquid phase-oxidizing an m-alkyl benzene.

Usually, a benzene dicarboxylic acid is produced by oxidizing the corresponding dialkyl benzene. For example, isophthalic acid is produced by liquid-phase oxidizing an m-alkyl benzene.

British Patent No. 1,555,246 discloses a process for producing isophthalic acid comprising liquid phase-oxidizing m-xylene in an aliphatic carboxylic acid, such as acetic acid in the presence of a catalyst comprising cobalt, manganese and bromine. In addition, U.S. Pat. No. 3,974,214 and Belgian Patent No. 871044 disclose a process of producing isophthalic acid comprising liquid phase-oxidizing m-xylene in the presence of the above catalyst and an aldehyde or ketone as an oxidation promoter.

British Patent No. 1,577,544 discloses liquid phase oxidation of m-xylene in a solvent other than acetic acid, or a process for producing isophthalic acid which comprises liquid phase-oxidizing m-xylene in an aqueous solution of benzoic acid in the presence of a catalyst comprising cobalt, manganese and bromine. In addition, U.S. Pat. No. 4,259,522 discloses a process for producing isophthalic acid which comprises oxidizing m-toluic acid in an aqueous solution in the presence of a catalyst comprising cobalt and manganese.

With the recent advances in industrial technology, the requirements to be satisfied by polymer products as engineering materials have become increasingly stringent and there is a demand for isophthalic acid that has sufficient purity and whiteness to justify use as a starting material for the manufacture of polymers. However, the isophthalic acid which has been produced according to the prior methods contains a large amount of impurities, such as 3-carboxy benzaldehyde (hereinunder referred to as 3CBA), etc. The polymers derived from the isophthalic acid containing a large amount of impurities have poor color. Such polymers were not suitable as engineering materials. Therefore, it was necessary to purify the isophthalic acid for preparing the engineering polymer materials. British Patent Nos. 1,152,575 and 1,152,576 disclose a process for purifying crude isophthalic acid which comprises hydrogenating the impurities of the crude isophthalic acid in the presence of a palladium catalyst at a high temperature in a state of an aqueous solution. That is, water is used as a reaction medium in the inventions given in British Patent Nos. 1,152,575 and 1,152,576. However, water which is an inert solvent in the references is not necessarily a good solvent for organic substances. Therefore, when crude isophthalic acid is contacted with a noble metal catalyst in water, impurities, such as toluic acid, which is a reduction product of 3CBA in the crude isophthalic acid and the like are likely to be incorporated into the purified isophthalic acid and as a result the color of the polymers derived from the isophthalic acid could not sufficiently be improved.

British Patent No. 1,152,575 describes improvement in crystallizing step in order to prevent the incorporation of impurities, e.g. toluic acid into the isophthalic acid. Such a process makes the operation and the apparatus therefor complicated, and as a result the process is not economical. In addition, toluic acid and isophthalic acid are incorporated into the mother liquor from which isophthalic acid crystal has been separated, and are discharged with the mother liquor. This not only lowers the yield of isophthalic acid, but also the toluic acid and the isophthalic contained in the exhaust solution causes water pollution. Therefore, it becomes necessary to treat the exhaust solution in order to prevent water pollution.

SUMMARY OF THE INVENTION

The above problems can be overcome by purifying crude isophthalic acid according to the present invention. That is, crude isophthalic acid containing a large amount of impurities, such as 3CBA can be purified by simple operation according to the present invention. Therefore, the present process can be carried out on an industrial scale, and provides an economically excellent process for producing highly pure isophthalic acid.

The present inventors found that acetic acid is a good solvent for impurities, e.g. organic impurities contained in crude isophthalic acid, and then found that when the oxidation reaction solution of an m-dialkyl benzene is catalytically hydrogenated in a hydrous acetic acid solvent containing definite amount of water, the impurities contained in the crude isophthalic acid can be removed. This invention is based on this discovery.

This invention relates to a process for producing highly pure isophthalic acid, characterized by contact-treating crude isophthalic acid, which has been obtained by liquid phase-oxidation, with a noble metal catalyst belonging to the Group VIII of the Periodic Table supported on activated carbon in a hydrous acetic acid solvent containing 1-50% by weight of water in the presence of hydrogen at 170°-300° C.

The crude isophthalic acid can be prepared by liquid phase oxidation of an m-dialkyl benzene with molecular oxygen in an acetic acid solvent in the presence of a heavy metal catalyst. After the crude isophthalic acid is contact-treated with a noble metal catalyst belonging to the Group VIII of the Periodic Table supported by activated carbon in the presence of hydrogen, the isophthalic acid thus treated is cooled and the deposited isophthalic acid is separated. The separated mother liquor is filtration-treated and recirculated into the liquid phase oxidation reaction step.

DETAILED DESCRIPTION OF THE INVENTION

The crude isophthalic acid to be purified according to the present invention can be prepared by liquid phase-oxidizing an m-dialkyl benzene according to the well known methods. According to the present invention, the mother liquor, from which isophthalic acid crystal has been separated can be used as a solvent for liquid phase oxidation of an m-dialkyl benzene, so the liquid phase-oxidation is preferably carried out in acetic acid. The liquid phase-oxidation of an m-dialkyl benzene is usually carried out with molecular oxygen in an acetic acid solvent in the presence of a heavy metal such as cobalt, manganese, etc., or the heavy meal and a bromine compound. For example, the oxidation may be carried out with air in an acetic acid or a hydrous acetic acid in the presence of a heavy metal, such as cobalt or manganese and a bromine compound at 150°–240° C. and 10–30 atms. The oxidation may be carried out with oxygen in the presence of a cobalt catalyst at 100°–150° C. and 5–20 atms. An oxidation promoter, such as acetaldehyde or methyl ethyl ketone can be used.

A typical example of m-dialkyl benzenes which are starting materials for the oxidation is m-xylene. However, the substituents are not limited to only methyl group, and may be an ethyl, n-propyl or i-propyl group, or aldehyde or acetyl group which can be oxidized to a carboxyl group. One of the two substituents may be a carboxyl group.

Many impurities, such as 3CBA are contained in the crude isophthalic acid obtained by liquid phase oxidation. The 3CBA content in the crude isophthalic acid to be purified according to the present invention is not critical. The loss of acetic acid can be suppressed by selecting such conditions that the 3CBA content becomes high in the preparation of crude isophthalic acid. Therefore, it is preferable from an industrial point of view to use such conditions that the 3CBA content in the isophthalic acid amounts to more than 500 ppm.

In the present invention, the crude isophthalic acid thus obtained is dissolved in a hydrous acetic acid with a definite concentration, and the resulting solution is contact-treated with a noble metal belonging to the Group VIII of the Periodic Table supported on activated carbon in the presence of hydrogen at pressurized pressure and high temperature.

Examples of the noble metals belonging to the Group VIII of the Periodic Table include palladium, platinum, ruthenium and rhodium. Palladium and platinum are preferable. A mixture of these metals may also be used.

Coconut shell activated carbon is preferable as the form of activated carbon. The amount of the catalyst metal to be supported on activated carbon may be in the range of 0.1–5% by weight. The catalyst in the above amount is used in order to exhibit its effect for a long time.

A hydrous acetic acid is used as a solvent for catalytic hydrogenation. The water content in the acetic acid solution is in the range of 1–50% by weight. When the hydrous acetic acid with such water content is used, the action of acetic acid can sufficiently be exhibited. When the acetic acid with such a concentration is used, highly pure isophthalic acid having excellent color characteristics can be obtained. Since a hydrous acetic acid is used in the present invention, solubility of isophthalic acid at a high temperature increases and loss of acetic acid due to hydrogenation can be suppressed. Highly pure isophthalic acid can very economically be obtained according to the present invention.

When the water content in the hydrous acetic acid is more than 50% by weight, impurities are likely to be incorporated into the isophthalic acid product to make the color of the isophthalic acid worse, because the solubility of the impurities in crystallizing step is lowered. In addition, since the water content in the mother liquor from which the isophthalic acid crystal has been separated is high, it becomes necessary to remove water from the mother liquor for reusing the mother liquor.

The catalytic-hydrogenation of crude isophthalic acid is carried out at a high temperature and a high pressure in order to carry out the operation in a solution state. The temperature at which the catalytic-hydrogenation is carried out is in the range of 170°–300° C., preferably 180°–250° C. The solubility of isophthalic acid in the solvent depends on the temperature. When the temperature is less than 170° C., only the isophthalic acid solution with lower concentration can be treated. This is not preferable from an industrial point of view. When the temperature is more than 300° C., by-reactions occurs and acetic acid is decomposed by action of hydrogen.

The concentration of isophthalic acid in the solution may be in the range of 10–30% by weight. The concentration of isophthalic acid should be selected within such a range that the isophthalic acid is completely dissolved in the solvent at a temperature of catalytic-hydrogenation.

The pressure at which the catalytic-hydrogenation is carried out may be the one for maintaining the solvent in a solution state, and for keeping a hydrogen partial pressure which is suitable for catalytic-hydrogenation. The pressure may usually be in the range of 15–50 kg/cm$^2$.

The amount of hydrogen employed may be supplied by at least 2 mol per 1 mol of 3CBA.

The reaction time may be the one for which the hydrogenation reaction substantially proceeds. The reaction time may usually be in the range of 1–300 minutes, and preferably 2–120 minutes.

The catalytic-hydrogenation may be carried out batch-wise or continuously.

When the crude isophthalic acid is catalytic-hydrogenated, 3CBA is converted to m-toluic acid, and similarly other tinting impurities are converted to materials which are soluble to acetic acid. The isophthalic acid solution which was catalytic-hydrogenated is cooled to deposit isophthalic acid crystal. The isophthalic acid crystal is separated from the mother liquor. The separated crystal is washed with acetic acid and dried to obtain highly pure isophthalic acid having an excellent degree of whiteness.

The mother liquor from which isophthalic acid has been separated can be used as a solvent for liquid phase oxidation for preparing crude isophthalic acid. The isophthalic acid and m-toluic acid contained in the mother liquor can be recovered as crude isophthalic acid in the oxidizing step of an m-dialkyl benzene. However, the mother liquor is filter-treated for removing finely divided catalyst powder, before the mother liquor is reused as a solvent for the oxidizing step of an m-dialkyl benzene.

The filter-treatment may be preferably carried out by allowing the high temperature mother liquor after catalytic-hydrogenation to pass through porous filter. The filter-treatment is carried out for preventing the catalyst powder from being incorporated into the isophthalic acid product; and for preventing the noble metal catalyst powder from being introduced into the oxidizing step of an m-dialkyl benzene. When the catalyst powder for hydrogenation is introduced into the oxidizing step, the noble metal catalyst strongly inhibits the oxidation reaction. The filter-treatment of the mother liquor may be carried out by using a filter formed of a porous material having an opening size of 0.1–20 μm. When the filtration is carried out at high temperature, porous materials such as carbon, ceramics, glass, sintered metal, etc. are preferable as a corrosion resistant material.

Since the mother liquor is resued as a solvent for the oxidation reaction, not only can the isophthalic acid and m-toluic acid contained in the mother liquor be recovered as crude isophthalic acid, but acetaldehyde, ethanol, ethyl acetate, etc. which are hydrogenation products of acetic acid are also oxidized to acetic acid.

EFFECTIVENESS OF THE INVENTION

According to the present invention, isophthalic acid that has sufficient purity and whiteness to justify use as a starting material for the manufacture of polymers, such as unsaturated polyester resin, alkyd resin, thermal resistant polyamide, etc. can be easily obtained on an industrial scale.

Since the mother liquor after catalytic-hydrogenation is recirculated into the oxidized step in the present invention, it becomes unnecessary to treat the exhaust solution for disposal.

In the present invention, 3CBA which is a by-product in the oxidizing step is reduced to m-toluic acid in the catalytic-hydrogenation. The m-toluic acid is oxidized to isophthalic acid which then recovered. Therefore, the yield of the isophthalic acid is improved.

EXAMPLE

The present invention is further explained by the following non-limiting examples and control runs. In the examples and control runs, the reaction conditions, the components employed and the properties of the resulting isophthalic acid are shown in Table 1.

The color tone of the purified isophthalic acid was measured by the following methods:

Optical Density ($OD_{400}$)

Absorbance of wave length of 400 m$\mu$ in a solution of N,N'-dimethyl formamide containing isophthalic acid with 20% concentration was measured by using a cell of 5 cm.

Resin Color (Hazen)

Isophthalic acid, fumaric acid, neopentyl glycol and propylene glycol (57:43:50:53 by mol) were copolymerized. The resin color of the styrene solution of the resulting resin (resin 60% by weight) was expressed as Hazen color index. The lower of the Hazen color index of the resin color, the better.

EXAMPLE 1

Crude isophthalic acid was obtained by liquid phase-oxidizing m-xylene by the following method Into a 2 liter titanium oxidation reactor equipped with an agitator, a reflux condenser, a heating means, an inlet for starting material, an air inlet, an exit for exhaust gas and an inlet for liquid recirculated were charged cobalt acetate tetrahydrate (0.490 grams), manganese acetate tetrahydrate (1.929 g), 47% hydrobromic acid (1.694 g) and acetic acid (1095.9 g) having a water content of 10%. (Catalyst concentration to hydrous acetic acid is cobalt 105 ppm, manganese 394 ppm and bromine 715 ppm). The content was heated to 210° C. Meta-xylene was oxidized at 210° C. and 17 Kg/cm$^2$.G in the reactor while introducing m-xylene (220 g) into the reactor at a constant speed for 40 minutes and blowing air into the reactor. The amount of air blown was adjusted so that the oxygen concentration in the exhaust gas was being kept at about 2%. The blowing of air was discontinued 5 minutes after the introduction of m-xylene was completed. The reactor was cooled, and the reaction slurry was withdrawn from the reactor and was filtered to obtain a crystal. The crystal was washed with acetic acid and dried to obtain crude isophthalic acid (320.0 g).

The yield of the isophthalic acid was 93.0 mol %. The 3CBA content in the isophthalic acid was 1500 ppm.

The crude isophthalic acid was catalytic-hydrogenated

Into a 2 liter titanium reactor equipped with an agitator, a reflux condenser, a heating means, an inlet for starting material, an inlet for gas, an exit for reaction solution, an exit for exhaust gas, an inlet for liquid recirculated and an underriding titanium metal wire catalyst cage which is movable upward and downward with magnetic induction means were charged crude isophthalic acid (300 g) and acetic acid (1200 g) having water content of 10%. The gas in the reactor was purged with hydrogen gas, and the reactor was pressurized to 5 Kg/cm$^2$.G and was heated. Particulate palladium catalyst (0.5 wt %) supported on coconut shell activated carbon (18 g) having 4-8 mesh was used as a catalyst. The catalyst was placed into the catalyst cage. The catalyst cage was held at upper position to the surface of the reaction solution. When the reactor was heated to 230° C., the catalyst cage was moved downward so that the catalyst was completely immersed into the reaction solution. Hydrogen was brown at a speed of 0.6N liter/hr for 20 minutes at 230° C. and 30 Kg/cm$^2$.G. The catalyst was moved upward to the upper position from the surface of the reaction solution, and at the same time, blowing of hydrogen was discontinued. The reaction solution was cooled to 100° C. The reaction slurry was withdrawn from the reactor, and the crystal was filtered with a glass filter (Pore Symbol of 3; standard maximum opening size of 40-100 $\mu$m). The crystal was washed with acetic acid and dried to obtain highly pure isophthalic acid (287.4 g). Recovery ratio of isophthalic acid was 95.8% by weight.

The mother liquor was filter-treated and reused as a solvent for liquid phase oxidation of m-xylene The mother liquor was heated to 100° C. and was filter-treated by using a glass filter (Pore Symbol of 4; standard maximum opening size of 10-16 $\mu$m). The result was the same as the result obtained by using a fresh acetic acid.

The filter-treated mother liquor was reused as a solvent for liquid phase oxidation of m-xylene. As a result, the properties of the resulting isophthalic acid obtained by using the mother liquor was the same as those of the isophthalic acid obtained using fresh acetic acid. The yield of the isophthalic acid was increased to 331.4 g (theoretical yield of 96.3 mol %). The isophthalic acid and m-toluic acid contained in the filtrate were recovered as highly pure isophthalic acid.

In contrast, when the mother liquor was reused in the oxidation of m-xylene without carrying out the filter-treatment, the oxidation reaction proceeded very slowly. Isophthalic acid having large amount of impurities was obtained. The yield of isophthalic acid was 83 mol % and the crude isophthalic acid contained 2 mol % of 3CBA. Even when the isophthalic acid was catalytic-hydrogenated, highly pure isophthalic acid could not be obtained.

EXAMPLE 2

The procedure of Example 1 was repeated except that hydrous acetic acid having a water content of 20% by weight was used as a solvent.

Control Run 1

The procedure of Example 1 was repeated except that hydrous acetic acid having a water content of 60% by weight was used as a solvent.

Control Run 2

The procedure of Example 1 was repeated except that glacial acetic acid was used as a solvent.

Control Run 3

The procedure of Example 1 was repeated except that pure water was used as a solvent.

EXAMPLES 3-5

The procedures of Example 1 were repeated except that platinum catalyst (Example 3), ruthenium catalyst (Example 4) and rhodium catalyst (Example 5) were used as a catalyst.

TABLE 1

| | Example 1 | Example 2 | Control Run 1 | Control Run 2 | Control Run 3 | Example 3 | Example 4 | Example 5 |
|---|---|---|---|---|---|---|---|---|
| Catalyst for hydrogenation | Pd | Pd | Pd | Pd | Pd | Pt | Ru | Rh |
| Solvent for hydrogenation | hydrous acetic acid | hydrous acetic acid | hydrous acetic acid | gracial acetic acid | pure water | hydrous acetic acid | hydrous acetic acid | hydrous acetic acid |
| water concentration (wt %) | 10 | 20 | 60 | 0.3 | 100 | 10 | 10 | 10 |
| Quality of purified isophthalic acid | | | | | | | | |
| 3CBA ppm* | 30 | 15 | 20 | 90 | 50 | 20 | 30 | 30 |
| m-toluic acid ppm** | 20 | 10 | 200 | 10 | 400 | 20 | 10 | 10 |
| $OD_{400}$ | 0.015 | 0.010 | 0.040 | 0.030 | 0.089 | 0.017 | 0.042 | 0.040 |
| Resin color (Hazen) | 30 | 20 | 60 | 50 | 70 | 20 | 30 | 30 |

*Quantitatively measured by polarography.
**Purified isophthalic acid was methyl-esterified, and the content was quantitatively measured by gel chromatography.

What is claimed is:

1. A process for producing highly pure isophthalic acid which comprises (a) carrying out liquid phase oxidation of an m-dialkyl benzene with molecular oxygen in an acetic acid solvent in the presence of a heavy metal catalyst to form crude isophthalic acid, wherein step (a) take place at temperature conditions of 100°-240° C. and at pressure conditions of 5-30 atmospheres, (b) contact-treating the resulting crude isophthalic acid with noble metal catalyst belonging to the Group VIII of the Periodic Table supported by activated carbon in the presence of hydrogen, wherein step (b) take place at temperature conditions of 170° C.-300° C. and at pressure conditions of 15-50 $kg/cm^2 \cdot G$. and then (c) separating the deposited isophthalic acid crystal and (d) filtration-treating the separated mother liquor and (e) recirculating the mother liquor thus treated into the liquid phase oxidation step (a) for reusing as a solvent in step (a).

2. The process of claim 1 wherein the m-alkyl benzene is m-xylene.

3. The process of claim 1 wherein the noble metal is selected from the group consisting of Pt, Pd, Ru, Rh and mixtures thereof.

4. The process of claim 3 wherein the noble metal is selected from the group consisting of Pd and Pt.

5. The process of claim 1 wherein the activated carbon is coconut shell activated carbon.

6. The process of claim 1 wherein the filtration treatment of the mother liquor is carried out by using glass fiber.

* * * * *